(12) United States Patent
Norman et al.

(10) Patent No.: US 7,276,031 B2
(45) Date of Patent: Oct. 2, 2007

(54) SYSTEM AND METHOD FOR CLASSIFYING PATIENT'S BREATHING USING ARTIFICIAL NEURAL NETWORK

(75) Inventors: Robert G. Norman, New Windsor, NY (US); Indu A. Ayappa, New York, NY (US); David M. Rapoport, New York, NY (US)

(73) Assignee: New York University, New York, NY (US)

( * ) Notice: Subject to any disclaimer, the term of this patent is extended or adjusted under 35 U.S.C. 154(b) by 74 days.

(21) Appl. No.: 10/844,650

(22) Filed: May 12, 2004

(65) Prior Publication Data

US 2005/0256420 A1 Nov. 17, 2005

(51) Int. Cl.
*A61B 5/02* (2006.01)
(52) U.S. Cl. ........................... 600/538; 600/529
(58) Field of Classification Search ........ 600/533–534; 128/204.23
See application file for complete search history.

(56) References Cited

U.S. PATENT DOCUMENTS

| | | | |
|---|---|---|---|
| 4,655,213 A | 4/1987 | Rapoport et al. | |
| 5,065,756 A | 11/1991 | Rapoport | |
| 5,245,995 A | 9/1993 | Sullivan et al. | |
| 5,335,654 A * | 8/1994 | Rapoport | 128/204.23 |
| 5,433,193 A | 7/1995 | Sanders et al. | |
| 5,490,502 A | 2/1996 | Rapoport et al. | |
| 5,535,739 A | 7/1996 | Rapoport et al. | |
| 5,546,933 A | 8/1996 | Rapoport et al. | |
| 5,551,419 A | 9/1996 | Froehlich et al. | |
| RE35,339 E | 10/1996 | Rapoport | |
| 5,732,696 A | 3/1998 | Rapoport et al. | |
| 5,732,697 A * | 3/1998 | Zhang et al. | 600/300 |
| 5,740,795 A | 4/1998 | Brydon | |
| 5,803,066 A | 9/1998 | Rapoport et al. | |
| 5,953,713 A * | 9/1999 | Behbehani et al. | 706/16 |
| 6,015,388 A | 1/2000 | Sackner et al. | |
| 6,135,106 A | 10/2000 | Dirks et al. | |
| 6,142,952 A | 11/2000 | Behbehani et al. | |
| 6,165,133 A | 12/2000 | Rapoport et al. | |
| 6,192,886 B1 | 2/2001 | Rudolph | |
| 6,286,508 B1 | 9/2001 | Remmers et al. | |
| 6,290,654 B1 * | 9/2001 | Karakasoglu | 600/529 |
| 6,299,581 B1 | 10/2001 | Rapoport et al. | |
| 6,342,039 B1 | 1/2002 | Lynn et al. | |

(Continued)

OTHER PUBLICATIONS

"Economic Implications of the Diagnosis of Obstructive Sleep Apnea," Annuals of Internal Medicine, vol. 130, No. 6, pp. 533-534 (Mar. 16, 1999).

(Continued)

*Primary Examiner*—Robert L. Nasser
(74) *Attorney, Agent, or Firm*—Fay Kaplun & Marcia, LLP.

(57) ABSTRACT

Described is a method and system for analyzing a patient's breaths. The arrangement may include a sensor and a processor. The sensor detects data corresponding to a patient's breathing patterns over a plurality of breaths. The processor separates the detected data into data segments corresponding to individual breaths. Then, the processor analyzes the data segments using a pretrained artificial neural network to classify the breaths based on a likelihood that individual ones of the breaths include an abnormal flow limitation.

24 Claims, 6 Drawing Sheets

AIRFLOW TO AND FROM CPAP GENERATOR

U.S. PATENT DOCUMENTS

| | | |
|---|---|---|
| 6,349,724 B1 | 2/2002 | Burton et al. |
| 6,360,741 B2 | 3/2002 | Truschel |
| 6,397,845 B1 | 6/2002 | Burton |
| 6,398,739 B1 | 6/2002 | Sullivan et al. |
| 6,427,689 B1 | 8/2002 | Estes et al. |
| 6,488,634 B1 | 12/2002 | Rapoport et al. |
| 2001/0000346 A1 | 4/2001 | Ruton et al. |
| 2002/0014241 A1 | 2/2002 | Gradon et al. |
| 2002/0023645 A1 | 2/2002 | Zdrojkowski et al. |
| 2003/0000528 A1* | 1/2003 | Eklund et al. ......... 128/204.23 |

OTHER PUBLICATIONS

Fletcher et al., "Unattended Home Diagnosis and Treatment of Obstructive Sleep Apnea Without Polysomnography." Arch Fam Med, vol. 9, pp. 168-174 (Feb. 2000).

"Assessment and Management of Obstructive Sleep Apnea in Adults," Guidles & Protocols, Advisory Committee, British Columbia Medical Association, Ministry of Heath and Ministry Responsible for Seniors, pp. 1-4 (Revised 2000).

Goodday et al., "Obstructive Sleep Apnea Syndrome: Diagnosis and Management" Journal of the Canadian Dental Association, vol. 67, No. 11, pp. 652-659 (Dec. 2001).

* cited by examiner

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

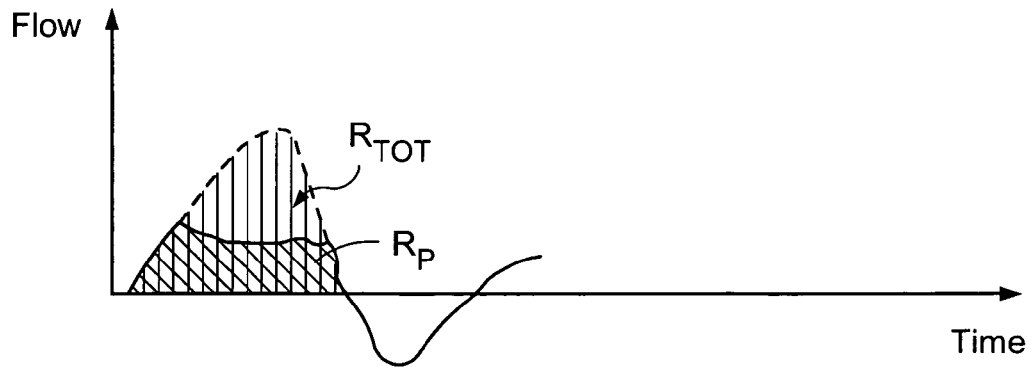
F I G. 8a
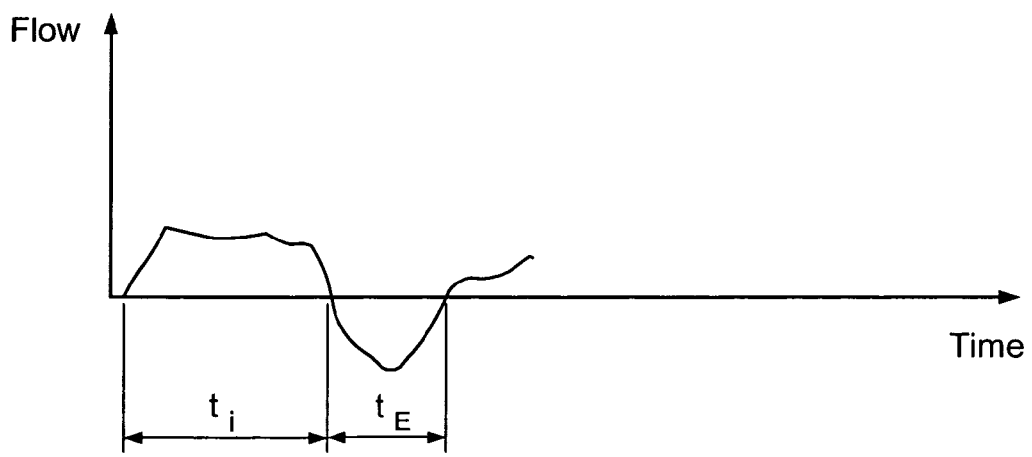
F I G. 8b
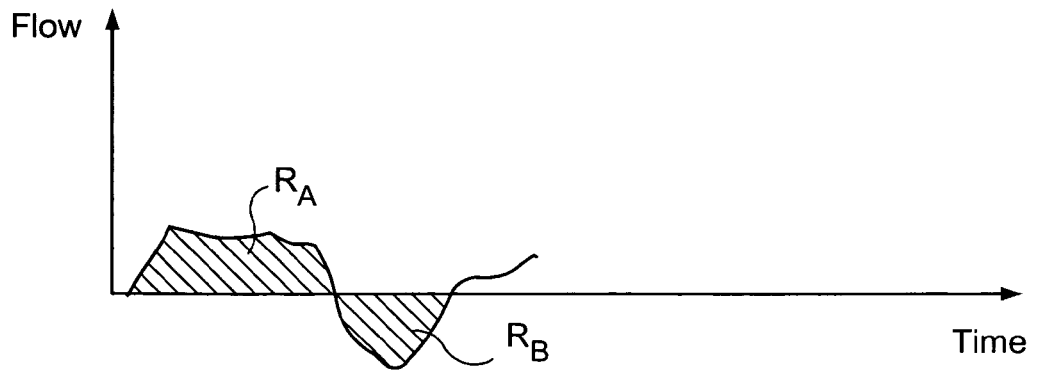
F I G. 8c

Table A

|   | A | B | C | D |
|---|---|---|---|---|
| A | 113 | 4 | 1 | 1 |
| B | 3 | 29 | 17 | 1 |
| C | 1 | 5 | 55 | 10 |
| D | 0 | 1 | 22 | 135 |

Fig. 9

SYSTEM AND METHOD FOR CLASSIFYING PATIENT'S BREATHING USING ARTIFICIAL NEURAL NETWORK

GOVERNMENT LICENCE RIGHTS

The U.S. Government has a paid-up license in this invention and the right in limited circumstances to require the patent owner to license others on reasonable terms as provided for by the terms of Grant No. K25 HL4420 awarded by the National Institute of Health.

BACKGROUND

Obstructive sleep apnea/hypopnea syndrome (OSAHS) is a well-recognized disorder that may affect as much as 1-5% of the adult population. OSAHS is one of the most common causes of excessive daytime somnolence. OSAHS is most frequent in obese males, and it is the single most frequent reason for referral to sleep disorder clinics.

OSAHS is associated with conditions in which there is anatomic or functional narrowing of the patient's upper airway, and is characterized by an intermittent obstruction of the upper airway occurring during sleep. The obstruction results in a spectrum of respiratory disturbances ranging from the total absence of airflow (apnea), despite continued respiratory effort, to significant obstruction with or without reduced airflow (hypopnea—episodes of elevated upper airway resistance, and snoring). Morbidity associated with the syndrome arises from hypoxemia, hypercapnia, bradycardia and sleep disruption associated with the respiratory obstructions and arousals from sleep.

The pathophysiology of OSAHS is not fully worked out. However, it is now well recognized that obstruction of the upper airway during sleep is in part due to the collapsible behavior of the supraglottic segment of the respiratory airway during the negative intraluminal pressure generated by inspiratory effort. The human upper airway during sleep behaves substantially similar to a Starling resistor which is defined by the property that flow is limited to a fixed value irrespective of the driving (inspiratory) pressure. Partial or complete airway collapse can then occur associated with the loss of airway tone which is characteristic of the onset of sleep and which may be exaggerated in OSAHS.

Starling resistor behavior is generally identified by the presence of an abnormal flow/pressure relationship. When the upper airway acts as a rigid tube (i.e., the normal state of the upper airway), flow is linearly related to a pressure difference across the upper airway. This relationship results in a substantially sinusoidal shape to a curve representing airflow in the airway over the time. When the upper airway exhibits Starling resistor behavior, the pressure/flow relationship changes. In particular, once the driving pressure decreases below a critical value, flow no longer increases in proportion to the pressure and a plateau develops on the pressure flow curve. This relationship produces a distinctive change in the shape of the inspiratory flow curve with respect to time. The detection of this abnormal shape of the inspiratory flow time curve, identifying an abnormal flow limitation, plays a critical role in both the diagnosis and treatment of OSAHS as it represents one of the least invasive means of detecting airway abnormalities.

Diagnosis of the spectrum of sleep disordered breathing requires the detection of all abnormal breathing events during sleep, including the occurrence of the abnormal inspiratory flow time contour indicative of Starling resistor behavior of the upper airway. While this may be performed by a human scorer, the automation of this analysis to provide rapid, reliable detection of such respiratory events is an important goal. Conventional apnea and hypopnea detection may be performed based on the analysis of signal amplitude alone. However, by definition, collapsible airway events showing Starling resistor behavior must be detected by other methods. Measurement of the pressure (drive) producing breathing is not practical in the majority of subjects requiring diagnosis.

Since 1981, positive airway pressure (PAP) applied by a tight fitting nasal mask worn during sleep has evolved as the most effective treatment for this disorder, and is now the standard of care. The availability of this non-invasive form of therapy has resulted in extensive publicity for sleep apnea/hypopnea and the appearance of large numbers of patients who previously may have avoided the medical establishment because of the fear of tracheostomy. Increasing the comfort of the system (e.g., by minimizing the applied nasal pressure) has been a major goal of research aimed at improving patient compliance with therapy.

In recent years, automatically adjusting PAP devices have been developed. These devices are designed to produce the appropriate PAP pressure needed to prevent obstructive respiratory events from occurring at each moment in time. The device may change the pressure (upward or downward) in response to characteristics of the patient's breathing. For example, the automatic PAP system must be able to accurately identify flow limitations and recognize them as indicative of a sleep disorder. Some systems have based flow limitation detection on empiric algorithms with user specified parameters that require adjustment for each patient to achieve optimal performance.

SUMMARY OF THE INVENTION

The present invention relates to a method and system for analyzing a patient's breaths. The arrangement may include a sensor and a processor. The senor detects data corresponding to a patient's breathing patterns over a plurality of breaths. The processor separates the detected data into data segments corresponding to individual breaths. Then, the processor analyzes the data segments using a pretrained artificial neural network to classify the breaths based on a likelihood that individual ones of the breaths include an abnormal flow limitation.

BRIEF DESCRIPTION OF THE DRAWINGS

The accompanying drawings which are incorporated in and constitute part of the specification, illustrate several embodiments of the invention and, together with the description, serve to explain examples of the present invention. In the drawings:

FIGS. 8a-8c show graphs illustrating patient's breathing pattern;

FIG. 9 shows an exemplary result generated by the system illustrated in FIG. 6.

DETAILED DESCRIPTION

FIGS. 1-5 illustrate waveforms of flow from a PAP generator, obtained during the testing of a patient in sleep studies. In these tests, the patient was wearing a PAP mask connected to an air source, for example, in the manner illustrated in U.S. Pat. No. 5,065,765. Each of these tests illustrates an epoch of 30 seconds, with the vertical lines depicting seconds during the tests. FIGS. 1-5 depict separate sweeps that were taken from 1 to 2 minutes apart, and with different pressures from the source of air.

Figure 1:
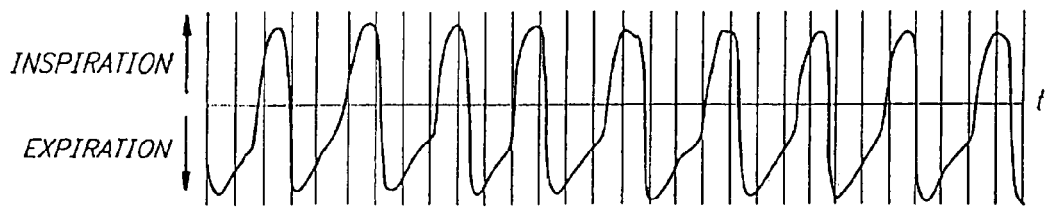
FIG. 1 shows a waveform of airflow from a sleeping patient in a 30 second epoch when subjected to a substantially constant PAP pressure of 10 cm H2O.

FIG. 1 illustrates a "normal" waveform, in this instance with a Continuous Positive Airway Pressure ("CPAP") of 10 cm H2O. Although this description uses a CPAP system to illustrate the system and method according to the present invention, those skilled in the art will understand that this invention is equally useful in conjunction with any of a variety of PAP systems supplying constant or varying pressure to patients. However, any other pressures identified as corresponding to apnea free respiration may also be used. It is noted that this waveform, at least in the inspiration periods, is substantially sinusoidal. The waveforms of FIGS. 2-5 illustrate that, as the controlled positive pressure is lowered, a predictable index of increasing collapsibility of the airway occurs, prior to the occurrence of frank apnea, periodic breathing or arousal.

Figure 2:
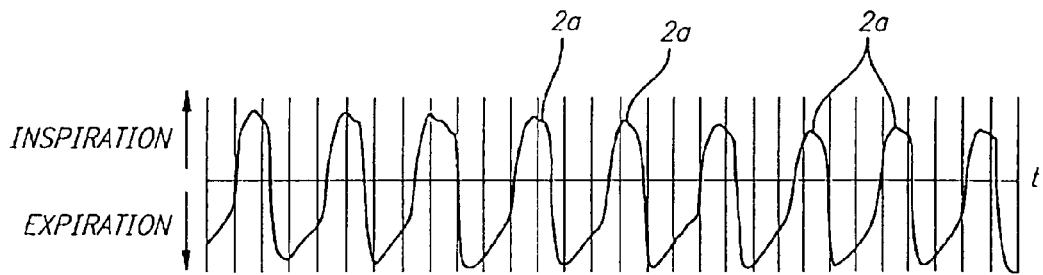
FIG. 2 shows a waveform of airflow from a sleeping patient in a 30 second epoch when subjected to a substantially constant PAP pressure of 8 cm H2O.
Figure 3:
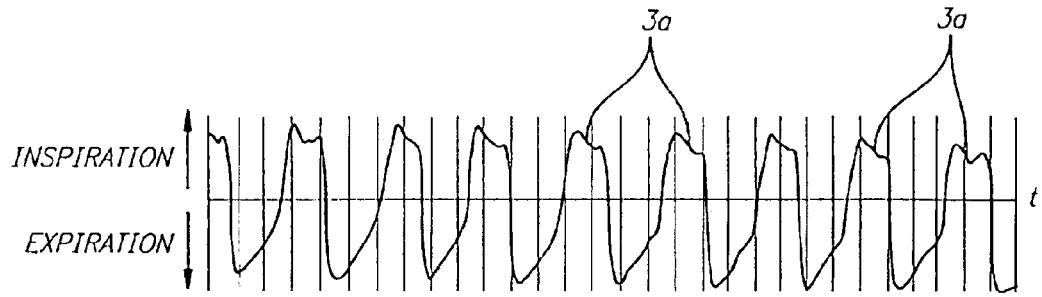
FIG. 3 shows a waveform of airflow from a sleeping patient in a 30 second epoch when subjected to a substantially constant PAP pressure of 6 cm H2O.
Figure 4:
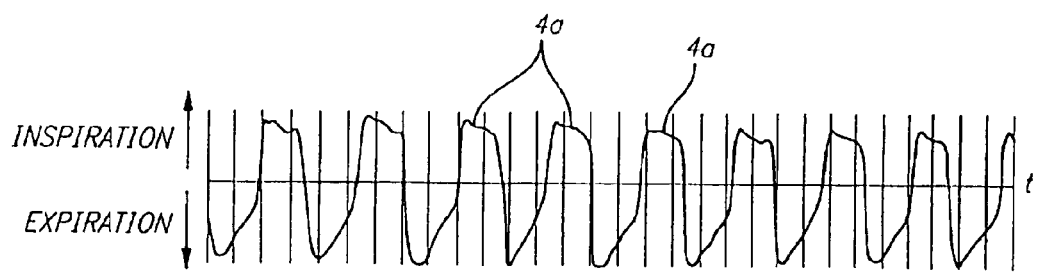
FIG. 4 shows a waveform of airflow from a sleeping patient in a 30 second epoch when subjected to a substantially constant PAP pressure of 4 cm H2O.
Figure 5:
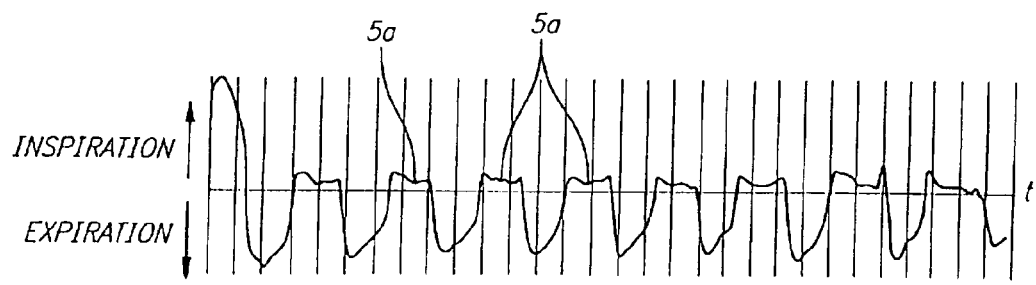
FIG. 5 shows a waveform of airflow from a sleeping patient in a 30 second epoch when subjected to a substantially constant PAP pressure of 2 cm H2O.

When CPAP pressure is decreased to 8 cm H2O, as illustrated in FIG. 2, a partial flattening of the inspiratory flow waveform, at region 2a, begins. This flattening becomes more definite when the controlled positive pressure is decreased to 6 cm H2O, as seen in region 3a of FIG. 3. The flattening becomes even more pronounced, as seen in region 4a of FIG. 4, when the controlled positive pressure is reduced to 4 cm H2O. These reductions in the CPAP pressure from the pressure of apnea free respiration, result in, for example, snoring or other signs of patient airway obstruction. When the CPAP pressure is further reduced to 2 cm H2O, as illustrated in FIG. 5, inspiratory flow may decrease to a virtually zero level during inspiratory effort as seen in region 5a. Shortly after the recording of the waveform of FIG. 5, the patient in the example developed frank apnea and awoke.

Figure 6:
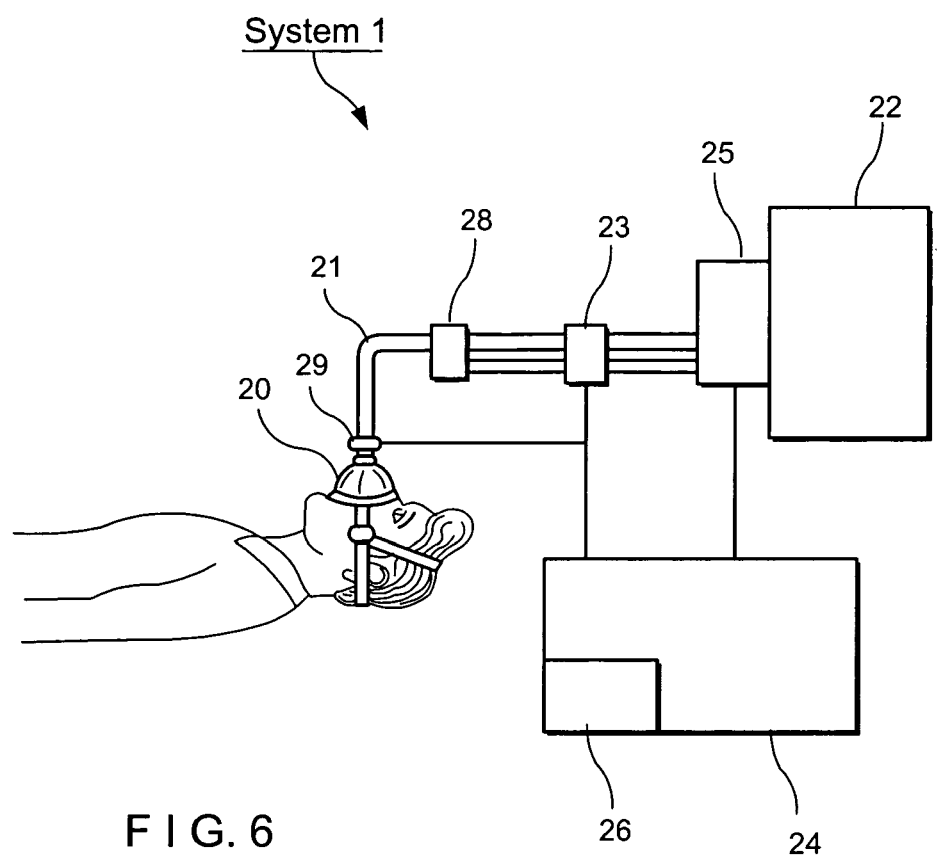
FIG. 6 shows an exemplary embodiment of a system according to the present invention.

FIG. 6 shows an exemplary embodiment of a system 1 according to the present invention. The system 1 may include a mask 20 which is connected, via a tube 21, to a flow generator 22. The mask 20 covers the patient's nose and/or mouth. A conventional flow sensor 23 is coupled to the tube 21 and detects both the airflow and the pressure in the tube 21. Signals corresponding to the airflow and the pressure are provided to a processing arrangement 24 for processing. The processing arrangement 24 outputs a control signal to a conventional flow control device 25 to control the pressure applied to the flow tube 21 by the flow generator 22. Those skilled in the art will understand that, for certain types of flow generators which may by employed as the flow generator 22, the processing arrangement 24 may directly control the flow generator 22, instead of controlling airflow therefrom by manipulating a separate flow control device 25.

The system 1 may also include a venting arrangement 28 which allows for gases exhaled by the patient to be diverted from the incoming air to prevent re-breathing of the exhaled gases. In an alternative exemplary embodiment of the present invention, the system 1 may include a further sensor 29 situated at or near the mask 20. The further sensor 29 is connected to the processing arrangement 24 and provides data regarding the airflow and the pressure in the mask 20.

Those skilled in the art will understand that the present invention may be utilized for the sole purpose of classifying the patient's breaths based on a likelihood that individual ones of the breaths include abnormal flow limitations. The abnormal flow limitation may be represented as a distinctive change in the shape of an inspiratory flow curve with respect to time. Alternatively, the present invention may be utilized for a plurality of functions such as the detection and diagnosis of sleep disorders (e.g., flow limitations), autotitration and/or treatment of such sleeping disorders, etc.

The system 1 also includes a neural network detection arrangement ("NNDA") 26 for analyzing a patient's data to generate output data classifying the patient's breaths as presence of the abnormal flow limitations. The NNDA 26 includes an artificial neural network which is constructed, trained, tested and utilized in accordance with the method of the present invention. Generally, the neural network is a system of programs and data structures that approximates the operation of the human brain. The neural network may involve a number of processors operating in parallel, each with its own small sphere of knowledge and access to data in its local memory. The neural network is initially "trained" using input data and rules about data relationships (e.g., data A in the range X-Y indicates certain flow limitations). In other words, the user trains the neural network how to behave in response to certain input data. The input data may be provided by a human operator, by environmental sensors or by other programs.

In making determinations, the neural network may use several principles, including gradient-based training, fuzzy logic, genetic algorithms and Bayesian methods. The neural network may be described in terms of knowledge layers with a number of such layers depending, for example, on how complex the neural network is. In the neural network, learned relationships concerning input data can "feed forward" to higher layers of knowledge. The neural network may also learn temporal concepts.

The neural network may consist, e.g., of a set of nodes including input nodes, output nodes, and hidden nodes operatively connected between the input and output nodes. There are also connections between the nodes with a number referred to as a weight associated with each connection. When the neural network is in operation, the input data is applied to each input node. Each input node then passes its given value to the connections leading out from it, and on each connection the value is multiplied by the weight associated with that connection. These connections lead to hidden nodes, with each hidden node in the next layer receiving a value which is the sum of the values produced by all of the connections leading into it. And in each hidden node, a simple computation is performed on the value—a sigmoid function is typical. This process is then repeated, with the results being passed through subsequent layers of hidden nodes until the output nodes are reached.

The neural network may use a plurality of calculation models. For example, some models may include loops where some kind of time delay process must be used; other models may be "winner takes all" models where the node with the highest value from the calculation fires and takes a value 1, and all other nodes take the value 0.

The weights in the neural network may be initially set to small random values; this represents a state in which the neural network knows nothing. As the training process proceeds, these weights converge to values allowing them to perform a useful computation. Thus, the neural network commences knowing nothing and moves on to gain real knowledge.

The neural network may be particularly useful for dealing with bounded real-valued data, where a real-valued output is desired; in this way, the neural network may perform classification by degrees, and is capable of expressing values equivalent to "not sure". When the neural network is trained using the cross-entropy error function and the neural network output is sinusoidal and non-linear, then the outputs may be used as estimates of a true posterior probability of a class.

Figure 10:
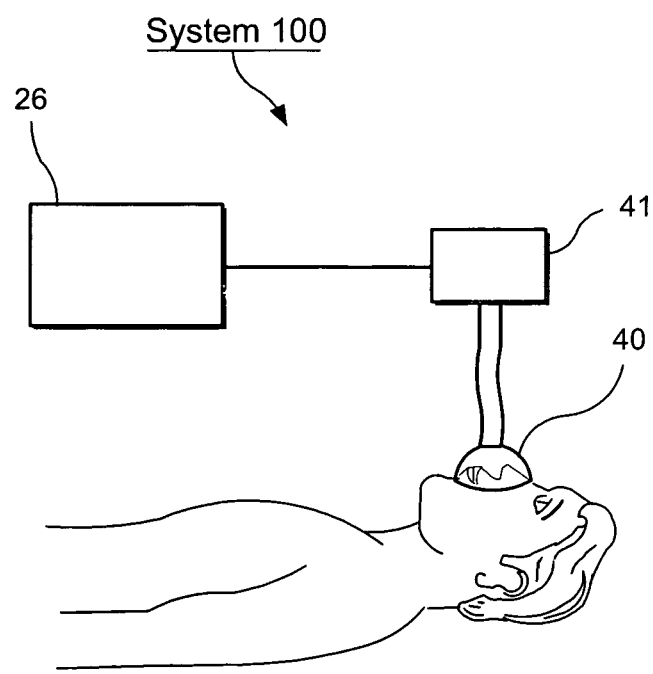
FIG. 10 shows another exemplary embodiment of a system according to the present invention.

Those skilled in the art will understand that although, the NNDA 26 is shown as a part of the processing arrangement 24, the NNDA 26 may be a stand-alone arrangement separate and apart from any PAP or CPAP system that treats the sleeping disorders. Furthermore, the NNDA 26 may be utilized (e.g., as shown in FIG. 10) for the sole purpose of diagnosis. In particular, FIG. 10 shows an exemplary embodiment of a system 100 according to the present invention. The system 100 measure patient's natural breaths (e.g., unassisted by the CPAP system). In particular, the patient's nose and/or mouth is covered with a mask 40 which is connected to a sensor 41. The sensor detects flow and/or pressure data for each of the patient's breaths. These data are converted into signals provided to the NNDA 26. Based on this data, the NNDA 26 generates output data classifying each corresponding breath of patient. Those skilled in the art would understand that instead of the mask 40, the user may utilize any arrangement that is capable of measuring/detecting flow in and out the patient's chest. Such an arrangement may include, for example, a nasal cannuala and pressure transducer, a derivative of the sum signal of a rib and abdominal impedance plethysmograph. The arrangement may also include a sensor in fluid communication with or other sensor of respiratory airflow.

Figure 7:
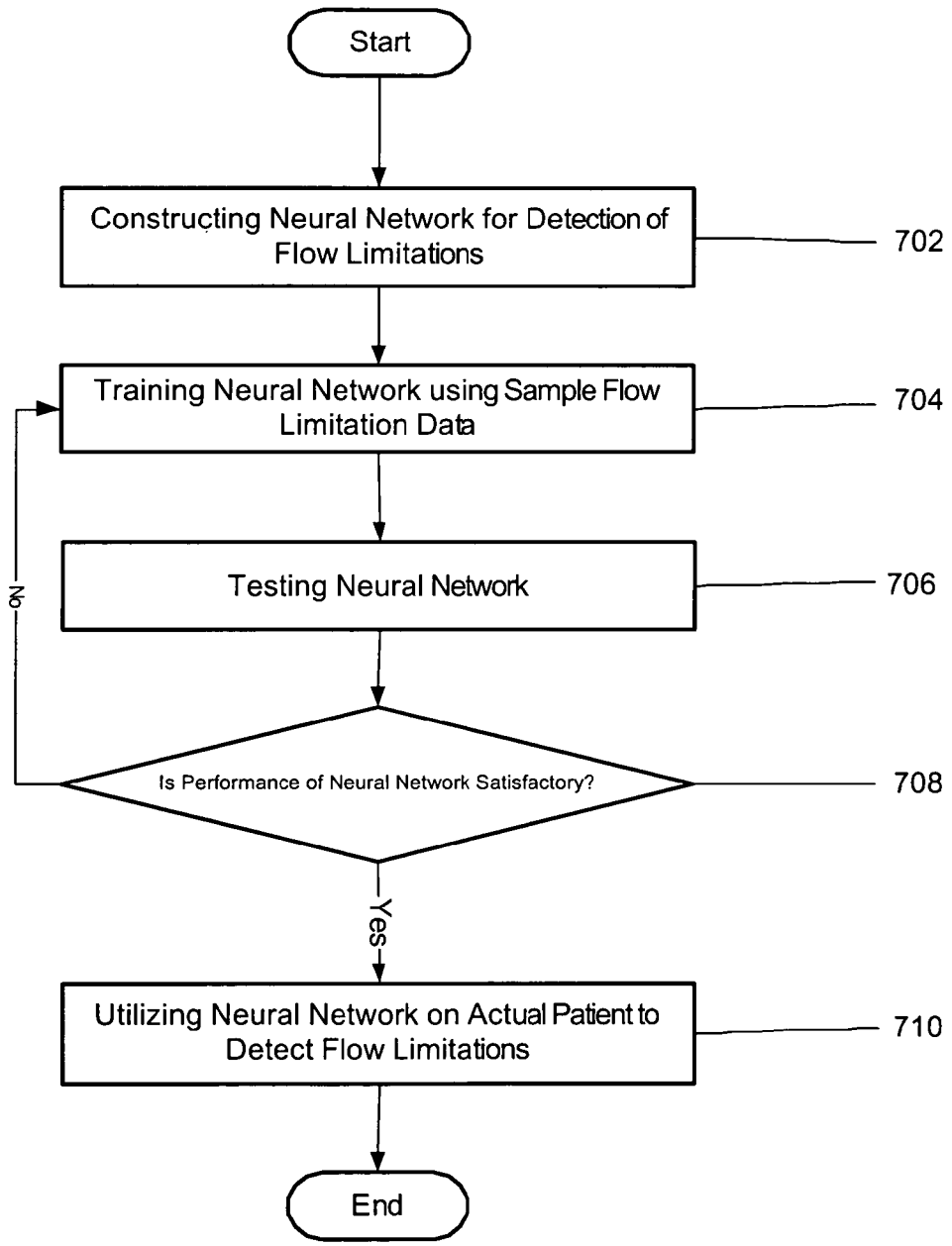
FIG. 7 shows an exemplary embodiment of a method according to the present invention.

FIG. 7 shows an exemplary embodiment of a method according to the present invention. In step 702, the user constructs an artificial neural network for the NNDA 26 which is capable of classifying each patient's breath and thus allows indication of abnormal flow limitations. The user then defines parameters for input data and output data. The input data may be generated based on certain digitized parameters for each breath (e.g., as shown in FIGS. 8b & 8c and as explained below). The output data may be, e.g., an indication as to whether or not the patient experiences abnormal flow limitations in each particular breath. Alternatively, the output data may classify each breath into four (4) categories: (1) a flow limitation is present; (2) a flow limitation is probably present; (3) a flow limitation is not probably present; and (4) a flow limitation is not present.

FIG. 8a shows exemplary input data $ID_1$ for the determination of the presence of a flow limitation:

$$ID_1 = [f_1, f_2, \ldots, f_n]$$

where f1, f2, ... fn are flow points which may be normalized and either evenly or unevenly spaced in time for each inspiration.

If the ID1 set describes a sinusoidal pattern, this may indicate healthy inspiration of the patient. On the other hand, if the ID1 array describes a non-sinusoidal shape, this may indicate that there are flow limitations in the patient's breathing which prevent the patient's inspiration from achieving the ideal sinusoidal shape.

FIG. 8b shows exemplary input data ID2 for the determination of the presence of abnormal flow limitations, where ID2 may be determined according to the following formula:

$$ID2 = TI/(TI+TE)$$

where TI is a time period of actual inspiration of the patient; and

TE is a time period of actual expiration of the patient.

If ID2 is at least equal to a critical value, for example, this may indicate that the patient's inspiration is healthy. On the other hand, if ID2 is less than the critical value, this may indicate that there are flow limitations in the patient's breathing.

FIG. 8c shows another exemplary input data ID3 for the determination of the presence of an abnormal flow limitation, where ID3 may be determined according to the following formula applied to mathematical functions of the airflow signal:

$$ID3 = RA/RB$$

where RA is an area under a curve representing a patient's inspiration above a critical threshold in the function of the airflow signal; and RB is an area under a curve representing a patient's inspiration below the critical threshold.

If ID3 is at least equal to a predetermined value, this may indicate healthy inspiration of the patient. On the other hand, if ID3 is less than the predetermined value, this may indicate that there are abnormal flow limitations in the patient's breathing. ID3 may be based, for example, on a first derivative of the digitized flow signal. Those skilled in the art will understand that additional input data may be generated based on a variety of mathematical transforms (e.g., a second derivative, a third derivative, etc.) of the digitized flow signal. In addition, those skilled in the art will understand that the area utilized for the calculation of ID3 may correspond to a complete breath of the patient, as well as a first half or a second half of a breath of the patient.

Those skilled the art will understand that there may be additional input data that may be utilized in determining whether the patient experiences abnormal flow limitations.

In step 704, the neural network is being trained to generated a calculating procedure. The training procedure may consist of the following substeps. First, the user generates input data based on a particular patient's breathing patterns. In particular, pressure and/or flow data for each of a patient's breaths is digitized and the input data, as described above, is generated.

The user then generates learning output data based on the patient's breathing patterns. In particular, the user analyzes the breathing patterns using conventional methods to determine whether or not the corresponding breath indicates abnormal patient flow limitations. For example, a physician may review the input data and manually classify each breath; based on this diagnosis, output data is generated. Once the input data and the learning output data have been generated, this data is provided to the neural network. The neural network analyzes the input data and the learning output data to generate the calculating procedure that arrives at the same results as the learning output data.

Those skilled in the art will understand that the quantity and quality of the input data and the consistency of the decision making in generating the learning output data will affect the accuracy of the neural network.

In step 706, a testing procedure is performed which allows a user to test the neural network. In particular, a new testing data set (including testing input data and testing output data) is generated by the user. The user then provides only the testing input data to the neural network and the neural network generates output data utilizing the calculating procedure. This output data is then compared to the testing output data to determine the accuracy of the neural network.

In step 708, a determination is made, based on predefined criteria, whether the performance of the neural network during the testing procedure is satisfactory to the user. For example, the user may specify that the output data of the neural network must be 98% accurate as compared to the testing output data. FIG. 9 shows an exemplary Table A which includes a comparison of the testing output data and the output data generated by the NNDA 26.

In particular, Table A has four columns and four rows, where A is a number of a patient's breaths that indicate the presence of abnormal flow limitations; B is a number of a patient's breaths that indicate the probable presence of abnormal flow limitations; C is a number of a patient's breaths that indicate the probable absence of abnormal flow limitations; and D is a number of a patient's breaths that indicate absence of abnormal flow limitations. The columns from the left to right include the results generated by the NNDA 26 and the rows from the top to bottom include the testing output data generated by the user.

In this particular case, Table A indicates that out of total of 398 instances, the NNDA 26 and the user had 332 identically classified instances (i.e., [A, A], [B, B], [C, C] and [D, D]) and 66 not identically classified instances (i.e., [A, B], [A, C], [B, A], [B, C], [B, D], [C, A], [C, B], [C, D], [D, A], [D, B], and [D, C]). In other words, the NNDA 26 was correct in 83.5% of the instances.

If this performance of the neural network is not satisfactory, the steps 704 and 706 are performed until the output data reach a satisfactory level of consistency with the testing output data.

In step 710, the neural network, which has already been trained and tested, receives patient's breathing flow pattern data to classify patient's breathes (e.g., to indicate presence of abnormal flow limitations). In particular, one of the sensors measures the patient's breathing flow and provides data corresponding to each breath to the processing arrangement 24 which digitizes the data and generates the input data. The generated input data is fed into the NNDA 26 which generates output data to classify each of the breaths.

According to one of the exemplary embodiments of the present invention, based on the output data, the system 1 shown in FIG. 6, may periodically (e.g., once a day or once a week) adjust the operation of the flow generator 22. In an alternative exemplary embodiment of the present invention, as shown in FIG. 10, the output data may be utilized by the user for diagnostic purposes.

It will be apparent to those skilled in the art that various modifications and variations can be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. An arrangement for analyzing a patient's breaths, comprising:
    a sensor detecting data corresponding to a patient's breathing patterns over a plurality of breaths; and
    a processor separating the detected data into data segments, each segment corresponding to an individual breath, the processor analyzing the data segments using a pretrained artificial neural network to classify each breath based on a likelihood that the breath includes an abnormal flow limitation,
    wherein the classifications include: (i) a flow limitation is present; (ii) a flow limitation is probably present; (iii) a flow limitation is not probably present; and (iv) a flow limitation is not present.

2. The arrangement according to claim 1, wherein the abnormal flow limitation includes a predefined change in the shape of an inspiratory flow curve with respect to time.

3. The arrangement according to claim 1, wherein the neural network is trained based on at least one set of input data and cone sponding output data, the output data being generated as a function of the input data and independently of the neural network.

4. The arrangement according to claim 3, further comprising:
    a flow generator providing a flow of air to the patient, the flow generator being controlled by the processor.

5. The arrangement according to claim 4, wherein, upon detecting the likelihood that an individual breath includes the flow limitation, the processor generates signals transmitted to the flaw generator to adjust the flow of air, the signals being generated by the processor as a function of output data.

6. The arrangement according to claim 1, further comprising:
    a venting arrangement allowing gases exhaled by the patient to be diverted from an incoming flow of air.

7. The arrangement according to claim 1, wherein the neural network is provided with first input data to generate first output data, the first output data being compared to second output data to generate an error margin value, the second output data being generated independently of the neural network.

8. The arrangement according to claim 7, wherein until the error margin value is greater than a predetermined error margin, the neural network is further trained with at least one set of training input and output data.

9. The arrangement according to claim 1, wherein each data segment is further broken into a set of flow points which characterizes a period of a patient's inspiration, and wherein if the set of flow points has a substantially sinusoidal pattern, the corresponding breath is classified as being free of the flow limitation.

10. The arrangement according to claim 1, wherein each data segment includes a first time period T1 of a patient's inspiration and a second time period T2 of a patient's expiration, wherein an indicator value ID is calculated according to the following formula: $ID=T1/(T1+T2)$, and wherein if the indicator value is above a predetermined value, the corresponding breath is classified as having the flow limitation.

11. The arrangement according to claim 1, wherein each data segment includes a first area RA of a patient's inspiration under a curve representing a patient's inspiration above a critical threshold and a second area RB under a curve representing the patient's inspiration below the critical threshold, wherein an indicator value ID is calculated according to the following formula: ID=RA/RB, and wherein, if the ID is at least equal to a predetermined value, the corresponding breath is classified as being free of the flow limitation.

12. The arrangement according to claim 1, wherein the classifications further include (v) an indeterminate classification in which the neural network is unable the classify the breath.

13. An arrangement, comprising:
a sensor detecting data corresponding to a patient's breathing patterns over a plurality of breaths;
an input device receiving control data corresponding to a desired diagnosis as to whether (i) a flow limitation is present; (ii) a flow limitation is probably present; (iii) a flow limitation is not probably present; and (iv) a flow limitation is not present in at least one of the breaths; and
a processor coupled to the sensor and the input device, the processor separating the detected data into data segments, each segment corresponding to an individual breath, the processor running an artificial neural network and processing the data segments and the corresponding control data to refine the neural network which processes the data segments to generate output data approximating the desired diagnoses.

14. A method for analyzing a patient's breaths, comprising the steps of:
obtaining data corresponding to a patient's breathing patterns over a plurality of breaths of the patient;
processing the detected data into data segments, each segment corresponding to an individual breath; and
analyzing each data segment using a pretrained artificial neural network to classify each breath based on a likelihood that the breath includes an abnormal flow limitation,
wherein the classifications include: (i) a flow limitation is present; (ii) a flow limitation is probably present; (iii) a flow limitation is not probably present; and (iv) a flow limitation is not present.

15. The method according to claim 14, further comprising the step of:
training the neural network based on at least one set of input data and corresponding output data, the output data being generated as a function of the input data and independently of the neural network.

16. The method according to claim 15, further comprising the step of:
providing to the patient a flow of air generated by a flow generator.

17. The method according to claim 16, flurther comprising the steps of:
upon detecting presence of the flow limitations in the individual breath, generating signals to adjust the flow of air as a function of the output data; and
transmitting the signals to the flow generator.

18. The method according to claim 14, further comprising the step of:
allowing, with a venting arrangement, gases exhaled by the patient to be diverted from an incoming flow of air.

19. The method according to claim 14, further comprising the steps of:
testing the neural ndwork by providing first input data and collecting first output data; and comparing the first output data to second output data to generate an error margin value, wherein the second control output data is generated independently of the neural network.

20. The method according to claim 19, further comprising the step of:
until the error margin value is greater than a predetermined error margin, further training the neural network using at least one set of training input and output data.

21. The method according to claim 14, further comprising the steps of:
further breaking each data segment into a set of flow points which characterizes a period of a patient's inspiration; and
if the set of flow points has a substantially sinusoidal patent, generating the output data indicative of absence of the flow limitation in the corresponding individual breath.

22. The method according to claim 14, further comprising the steps of:
calculating a first time period T1 of a patient's inspiration and a second time period T2 of a patient's expiration in each data segment;
determining an indicator value ID according to the following formula: ID=T1/(T1+T2); and
generating the output data indicative of the presence of the flow limitation in the corresponding individual breath if the indicator value is above a predetermined value.

23. The method according to claim 14, further comprising the steps of:
calculating, in each data segment, a first area RA of a patient's inspiration under a curve representing a patient's inspiration above a critical threshold and a second area RB under a curve representing the patient's inspiration below the critical threshold;
determining an indicator value ID) according to the following formula: ID=RA/RB; and
if the ID is at least equal to a predetermined value, generating the output data indicative of absence of the flow limitations in the corresponding individual breath.

24. A method, comprising the steps of:
detecting, with a sensor, data corresponding a patient's breathing patterns over a plurality of breaths of the patient;
receiving, with an input device, control data corresponding to a desired diagnosis as to whether (i) a flow limitation is present; (ii) a flow limitation is probably present; (iii) a flow limitation is not probably present; and (iv) a flow limitation is not present in at least one of the breaths;
separating, with a processor, the detected data into data segments, each segment corresponding to an individual breath, the processor running an artificial neural network; and
processing, with the processor, the data segments and the corresponding control data to refine the neural network which processes the data segments to generate output data approximating the desired diagnoses.

* * * * *